(12) United States Patent
Modglin (10) Patent No.: US 7,320,670 B1
(45) Date of Patent: Jan. 22, 2008

(54) BRACE AND STRAP SYSTEM

(75) Inventor: Michael D. Modglin, Braselton, GA (US)

(73) Assignee: DeRoyal Industries, Inc., Powell, TN (US)

( * ) Notice: Subject to any disclaimer, the term of this patent is extended or adjusted under 35 U.S.C. 154(b) by 248 days.

(21) Appl. No.: 11/129,936

(22) Filed: May 16, 2005

Related U.S. Application Data (63) Continuation-in-part of application No. 10/395,527, filed on Mar. 21, 2003, now Pat. No. 6,926,685.

(51) Int. Cl.
*A61F 5/00* (2006.01)
(52) U.S. Cl. .................................. 602/5; 602/19
(58) Field of Classification Search ............ 602/5, 602/19; 128/869, 876, 96.1, 100.1, 102.1–106; 2/311, 312, 321, 322; 24/306, 312, 442
See application file for complete search history.

(56) References Cited

U.S. PATENT DOCUMENTS

| | | | |
|---|---|---|---|
| 2,828,737 A | 4/1958 | Hale | |
| 4,005,506 A | 2/1977 | Moore | |
| 5,658,244 A | 8/1997 | Townsend et al. | |
| 5,911,697 A | 6/1999 | Biedermann et al. | |
| 6,363,936 B1 | 4/2002 | McCormick et al. | |
| 6,610,022 B1 | 8/2003 | Ashbaugh et al. | |
| 6,926,685 B1 * | 8/2005 | Modglin | 602/5 |
| 7,025,737 B2 * | 4/2006 | Modglin | 602/19 |
| 2002/0029406 A1 | 3/2002 | Meyer | |

FOREIGN PATENT DOCUMENTS

WO    WO 00/78168 A1    12/2000

* cited by examiner

*Primary Examiner*—Michael A. Brown
(74) *Attorney, Agent, or Firm*—Luedeka, Neely & Graham, PC (57) ABSTRACT

A brace and strap system including a brace having a posterior support having a substantially rigid posterior splint, an anterior support having a substantially rigid anterior splint. A strap system secures the supports in fitting engagement with the body parts of the user. The strap system includes a first strap and a first buckle located on the first strap, a second strap and a second buckle located on the second strap, a plurality of slides secured to a portion of the posterior support for receiving the straps, a first latch member secured to a first portion of the anterior support, and a second latch member secured to a second portion of the anterior support.

6 Claims, 11 Drawing Sheets

BRACE AND STRAP SYSTEM

CROSS-REFERENCE TO RELATED APPLICATIONS

This is a continuation-in-part of U.S. application Ser. No. 10/395,527 filed Mar. 21, 2003 and entitled STRAP SYSTEM now U.S. Pat. No. 6,926,685 and of co-pending U.S. application Ser. No. 10/738,796 filed Dec. 17, 2003 and entitled SPINAL BRACE HAVING OVERLAPPING RIGID MEMBERS.

FIELD OF THE INVENTION

This invention relates generally to braces and securement straps therefor. More particularly, this invention relates to a brace and strap system that is particularly useful for treating spinal conditions.

BACKGROUND AND SUMMARY OF THE INVENTION

Improvement is desired in the field of spinal braces and in the securement of such braces to the patient.

In a preferred embodiment, the invention relates to a brace and strap system. The brace includes a posterior support having a substantially rigid posterior splint, an anterior support having a substantially rigid anterior splint, and first and second overlapping supports releasably attachable to the posterior support. Each overlapping support has a substantially rigid splint.

A strap system is provided for securing the supports in fitting engagement with the body parts of the user. The strap system includes a first strap and a first buckle located on the first strap, a second strap and a second buckle located on the second strap, a plurality of slides secured to a portion of the posterior support for receiving the straps, a first latch member secured to a first portion of the anterior support, and a second latch member secured to a second portion of the anterior support.

BRIEF DESCRIPTION OF THE DRAWINGS

Further features of preferred embodiments of the invention will become apparent by reference to the detailed description of preferred embodiments when considered in conjunction with the figures, which are not to scale, wherein like reference numbers, indicate like elements through the several views, and wherein.

FIG. 7 is a perspective view of a strap system in accordance with another embodiment of the invention.

DETAILED DESCRIPTION

Figure 1:
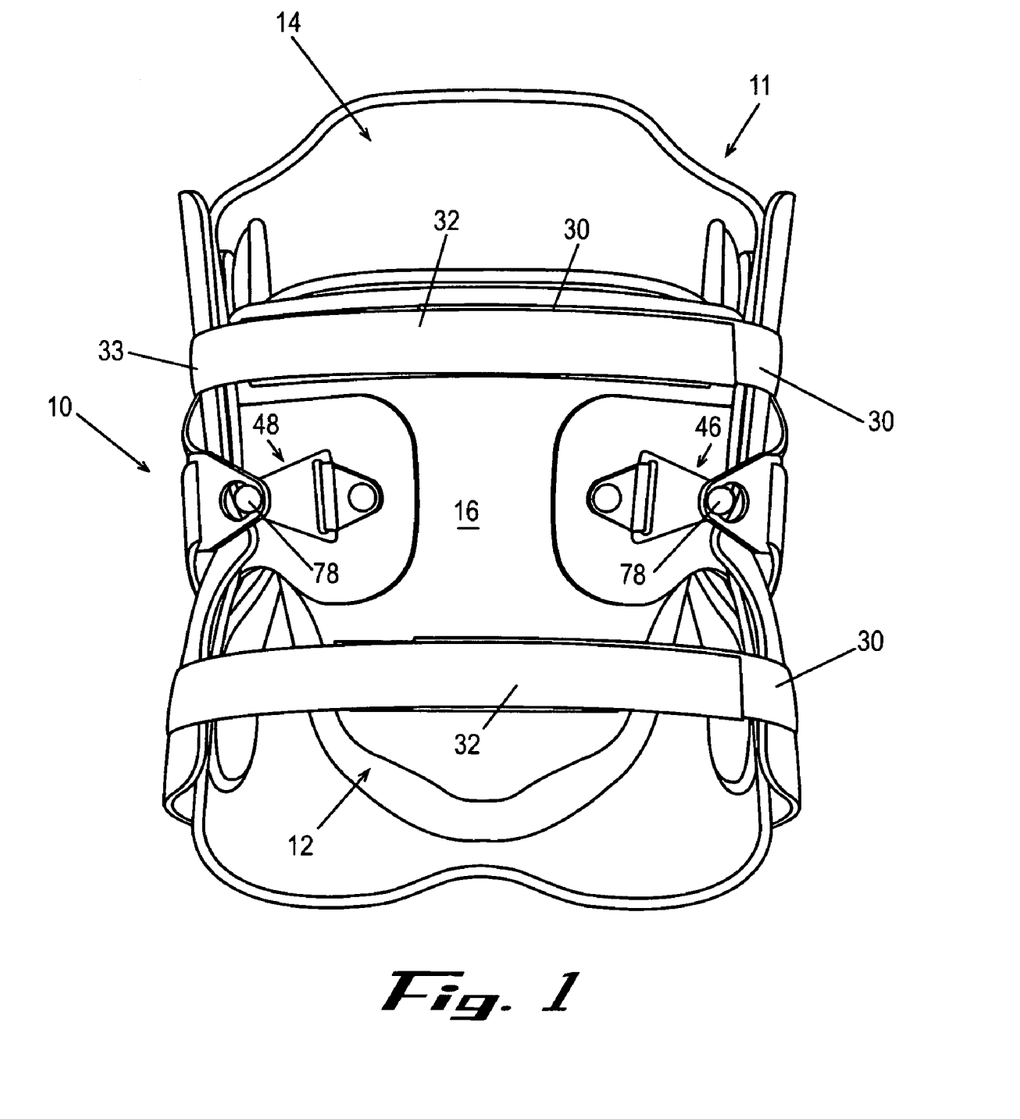
FIG. 1 is a front perspective view of a spinal brace utilizing a strap system in accordance with a preferred embodiment of the invention.
Figure 2:
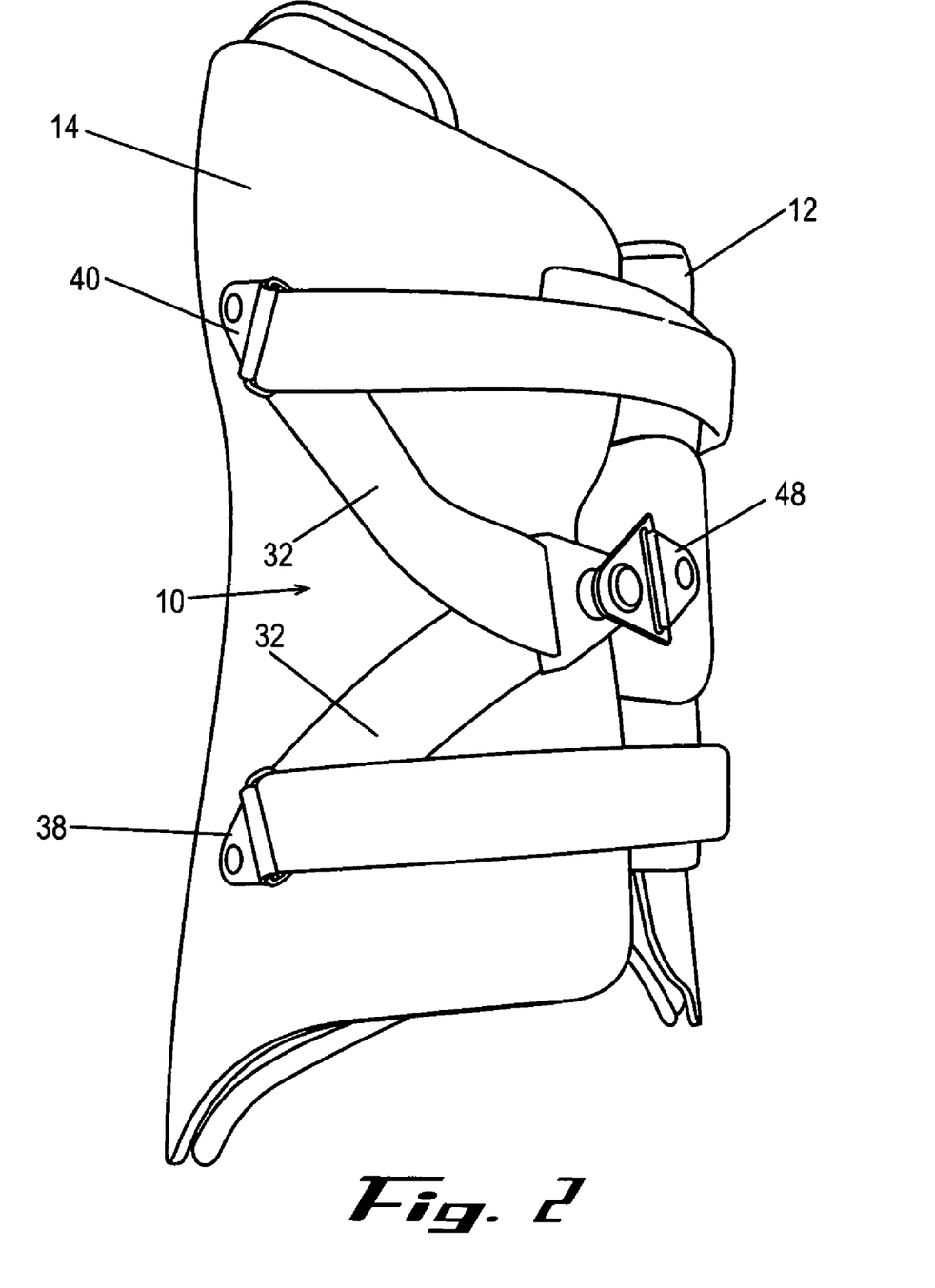
FIG. 2 is a side view of the brace and strap system of FIG. 1.
Figure 3:
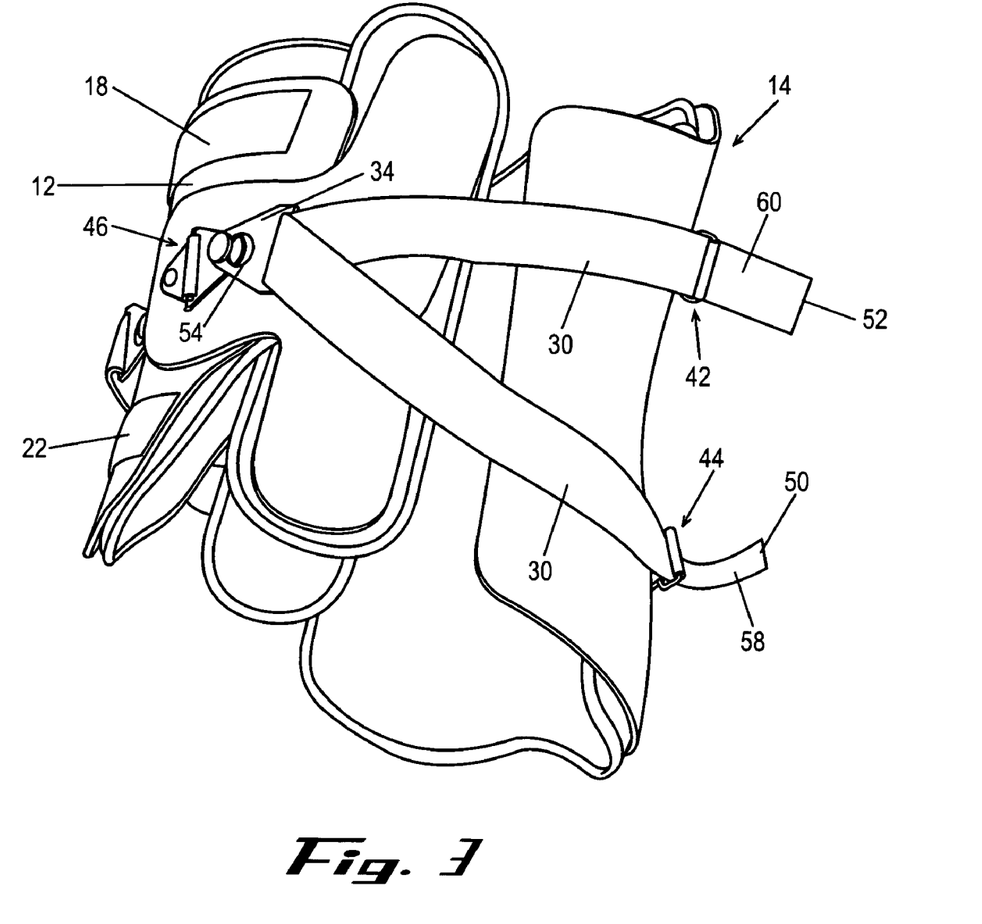
FIG. 3 is an exploded view of the brace and strap system of FIG. 1.
Figure 4:
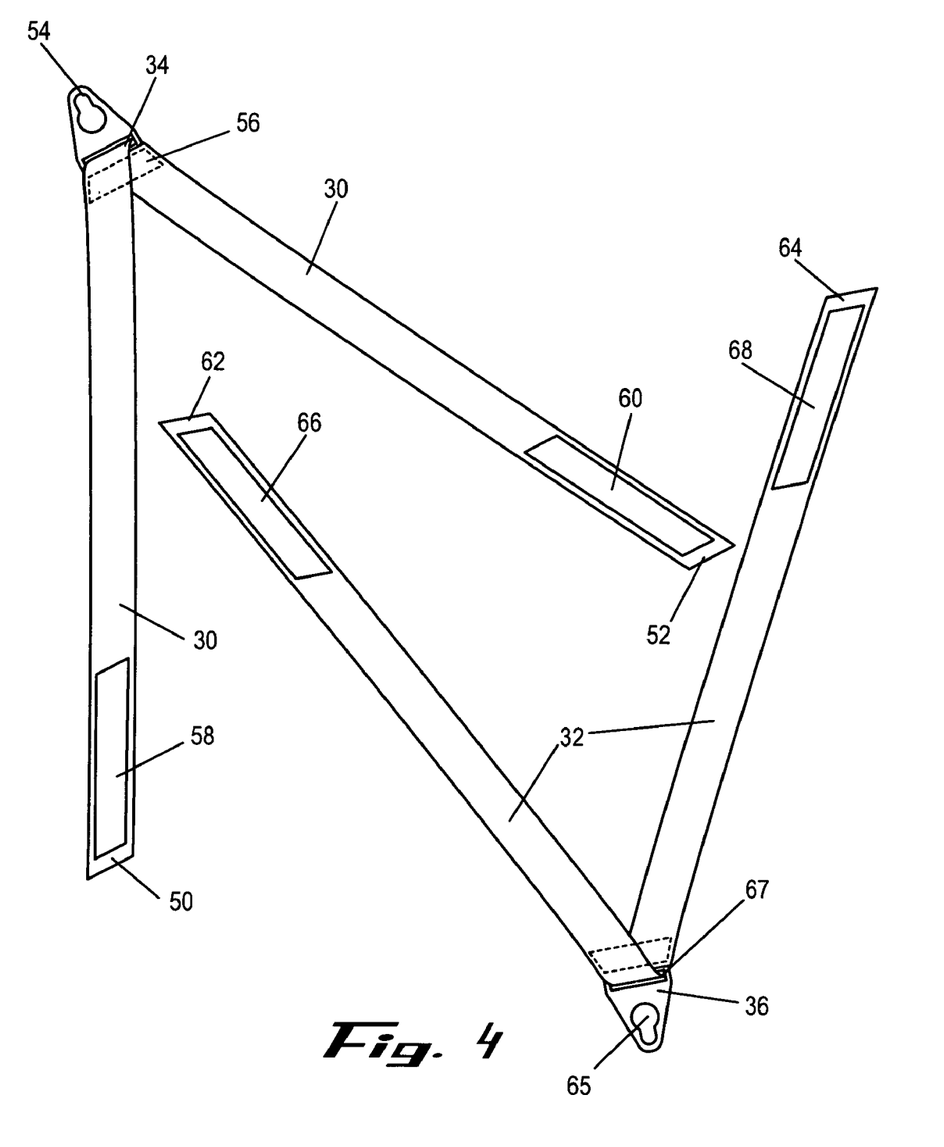
FIG. 4 is a plan view of strap components of a strap system in accordance with a preferred embodiment of the invention.
Figure 5:
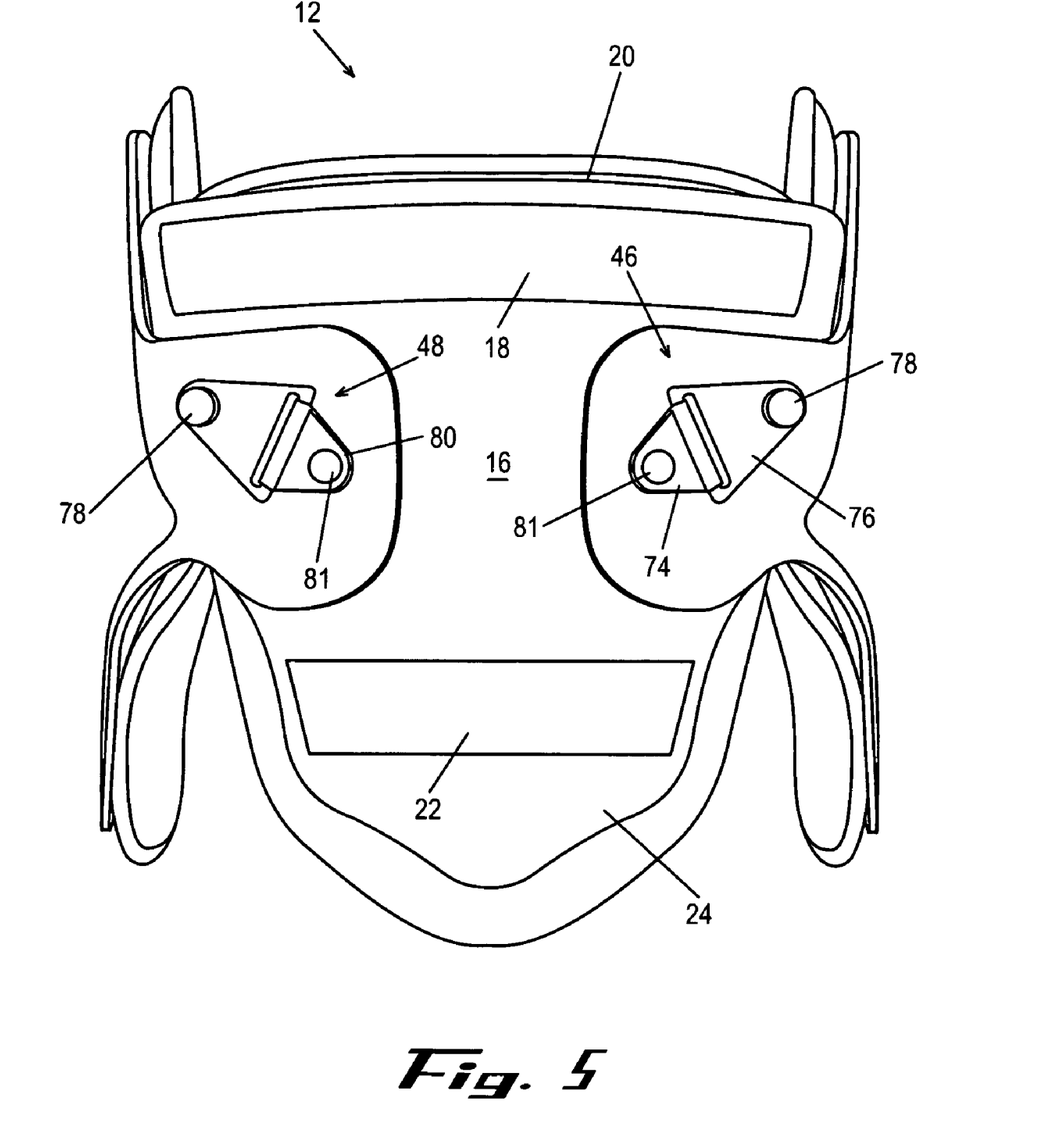
FIG. 5 is an exterior view of a front shell of the brace of FIG. 1 which shows components of the strap system attached to the front shell.
Figure 6:
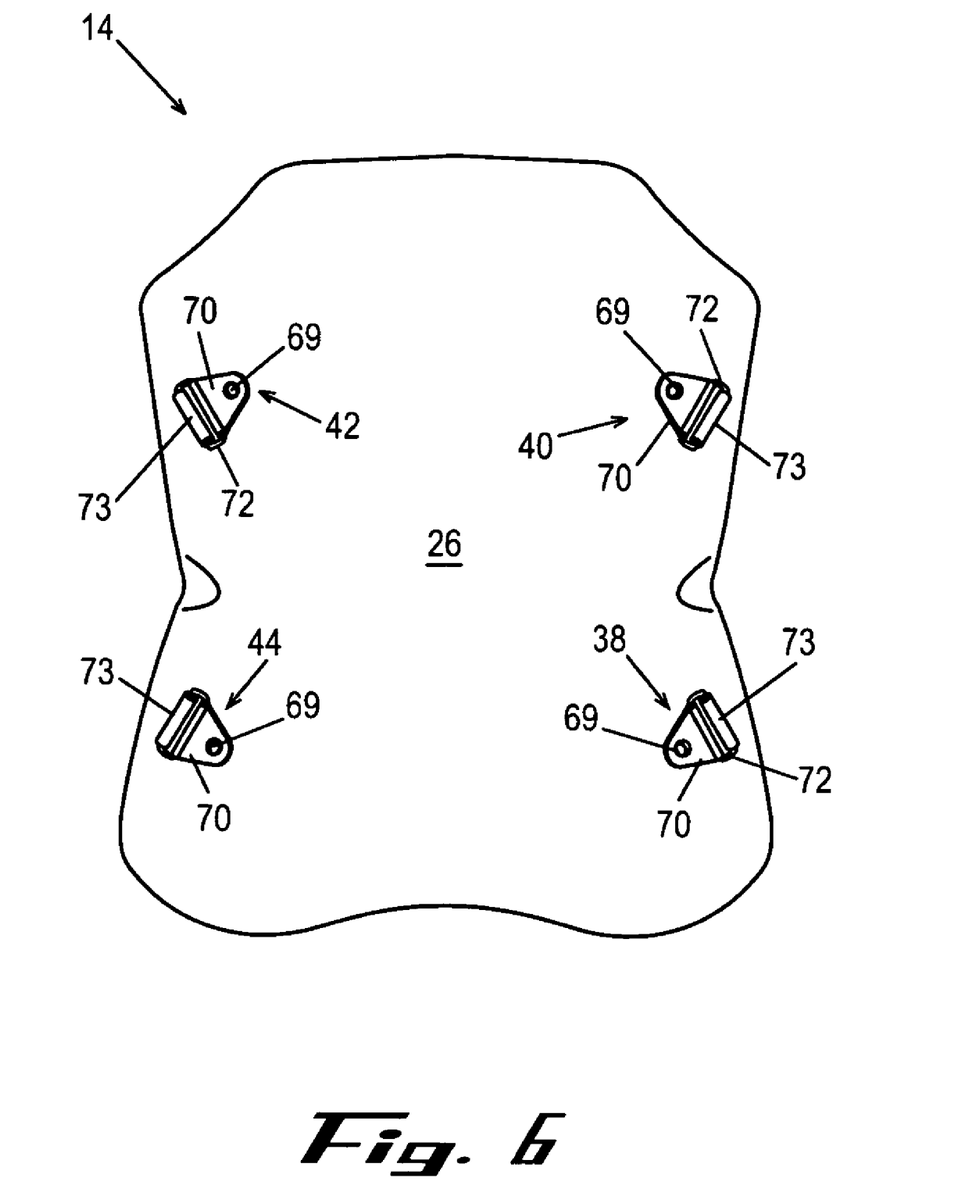
FIG. 6 is an exterior view of a rear shell of the brace of FIG. 1 which shows components of the strap system attached to the rear shell.

FIGS. 1-6

With initial reference to FIGS. 1-6, the invention relates to a strap system 10. For the purpose of example, the strap system 10 is shown for use with a spinal brace 11 having a front shell 12, and a rear shell 14. The brace 11 has shells 12 and 14 configured to serve as a lumbar-sacral orthosis (LSO). It will be understood, however, that the strap system 10 may be used with a variety of braces as well as in other applications. It is noted that the shells described herein are generally rigid shells of the type used for spinal braces. It will be understood that the shells could also be relatively flexible and of other than plastic construction, such as cotton or other fabric used for wrist braces and the like.

The depicted brace 11 is the subject of commonly assigned and co-pending application Ser. No. 10/395,763, entitled SPINAL BRACE, filed Mar. 21, 2003 (allowed, issue fee paid), incorporated herein by reference in its entirety.

The front shell 12 is of molded thermoplastic construction and includes an exterior surface 16. An elongate strip of material 18 having an outer surface configured of a loop or hook material of the type suitable for releasably engaging a hook material or loop material respectively is preferably secured, as by adhesive, substantially laterally across the exterior 16 surface of the shell 12 adjacent a first edge 20 thereof.

Likewise, an elongate strip of material 22 having an outer surface configured of a loop (or hook) material of the type suitable for releasably engaging a hook (or loop) material is preferably secured, as by adhesive, substantially laterally across the exterior surface adjacent a second edge 24. Alternatively, other attachment devices such as stitches, buttons, fasteners, and the like may be used.

The rear shell 14 is preferably made of the same material as the front shell 12 and preferably configured to partially overlap the front shell 12 when installed on a user. The shell 14 includes an exterior surface 26.

The strap system 10 includes a pair of straps 30 and 32, and a pair of buckles 34 and 36 fixedly secured on the straps 30 and 32. Slides 38, 40, 42, and 44 are attached to the exterior surface 26 of the rear shell 14, and latch members 46 and 48 are attached to side portions of the shell 12.

The strap 30 includes opposite ends 50 and 52 and has a suitable length which may preferably range from about 38 to about 48 inches for use with the spinal brace 11, although other lengths may likewise be suitable. The buckle 34 is preferably of one-piece plastic construction and includes a latching aperture 54 and a mounting slit 56. The strap 30 is passed through the slit 56 and the buckle 34 positioned at about the midpoint of the strap 30. The strap 30 is folded about itself and preferably secured, as by stitches or other fastening devices, to form the strap in a generally A-shape, with the buckle 34 fixedly located at the apex. A hook material 58 is preferably provided on the strap 30 adjacent the end 50 and a hook material 60 is preferably provided on the strap 30 adjacent the end 52.

The strap 32 is preferably identical to the strap 30 and is identically configured with regard to the buckle 36 and includes ends 62 and 64 and hook material 66 and 68. The buckle 36 is identical to the buckle 34, and likewise includes aperture 65 and a mounting slit 67.

The slides 38-44 are configured for receiving and slidably retaining the straps and are mountable to the shell 14 as by fasteners such as rivets 69 or the like. As will be seen, each slide 38-44 includes a mounting base 70 and an elongate loop 72 pivotally mounted to the base 70 and configured for passage of the straps 30 or 32 there through. A plastic cylinder 73 is preferably mounted on the loop 72 to serve as a roller to facilitate sliding of the straps. The internal diameter of the cylinder 73 is preferably larger than the diameter of the loop 72 so that the cylinder turns freely.

The latch members 46 and 48 each include a base 74 for mounting to the shell 12 and a latch 76 pivotally mounted to the base 74. The latch 76 is configured for releasably engaging the latching apertures 54 of the buckles 34 and 36, and preferably includes a mushroom-shaped projection 78 for releasably engaging the latching apertures 54 of the buckles.

The base 74 preferably includes an aperture 80 for passage of a fastener to secure the base to the exterior surface of the shell, such as threaded fastener 81. The fastener 81 may pass through an aperture provided through the shell and threadably engage a flanged threaded cylinder located adjacent the opposite surface of the shell.

The strap system 10 is utilized to secure the brace 11 in place after it is positioned on a user. The brace 11 is generally installed around the trunk of a user by placing the front shell 12 adjacent the front of the user and the rear shell adjacent the spine of the user, with the sides of the rear shell 14 overlapping the sides portion of the front shell 12. The buckles of the straps, such as buckle 34 of the strap 32, are secured to the latch members, such as latch member 48, as by engaging the latching aperture 48 around the projection 78. Also, the straps are passed through the slides, as by passing ends 50 and 52 through the slides 42 and 44.

The shells 12 and 14 may be urged toward one another as desired by pulling on the ends of each of the straps to place the ends adjacent the strips of loop material 48 and 50. The hook material associated with the ends of the straps is then matingly engaged with the loop material 18 and 22 attached to the exterior of the shell 12. As will be appreciated, the ends of the straps may be overlapped, as the exterior surfaces of the strap provide a loop material engageable with the hook material. Also, the location of the hook and loop material may be interchanged and/or other releasable fastening devices, such as snaps, buckles, and the like may be used to maintain the ends of the straps in place.

The strap system 10 is easier to use than conventional strap systems, and enables a user to conveniently secure a brace in place. The strap system 10 is also easily adjusted by a user to enable enhanced comfort benefits.

FIG. 7

Turning now to FIG. 7, there is shown a strap system 100 for use with a brace 102 having a shell 104. The shell 104 includes a slit 106 that enables the brace to be positioned around a body part of a user. The strap system 100 includes a strap 108, and buckle 110 fixedly secured on the strap 108. Slides 112 and 114 are attached to the exterior surface the rear shell 104, and a latch member 116 is attached to the shell 104. A pair of strips of loop (or hook) material 118 and 120 are attached to the shell 104, preferably on the same side of the slit 106 as the buckle 110.

The strap 108 is preferably substantially identical to the strap 30 and includes a pair of opposite ends 122 and 124, with hook material 126 and 128 located thereon adjacent the ends. The buckle 110 is preferably substantially identical to the buckle 34 and includes a latching aperture 130. The slides 112 and 114 are preferably substantially identical to the slides 38-44. The latch member 116 is preferably substantially identical to the latch member 46 and includes a projection for 132 for releasably engaging the latching aperture 130. The slides 112 and 114 and the latch member 116 are preferably secured to the shell 104 in a manner similar to that previously described for the latch member 46 and the slides 38-44.

The strap system 100 may be used in a manner similar to that described for the strap system 10. For example, the shell 104 is placed around a body part and the strap system 100 is used to maintain it in position and otherwise urge the shell against the body part. The ends 122 and 124 of the strap 108 are placed through the slides 112 and 114 and the buckle 110 engaged with the latch member 116. The ends 122 and 124 are then pulled to impart tension and placed in engagement with the hook material 118 and 120.

Figure 8:
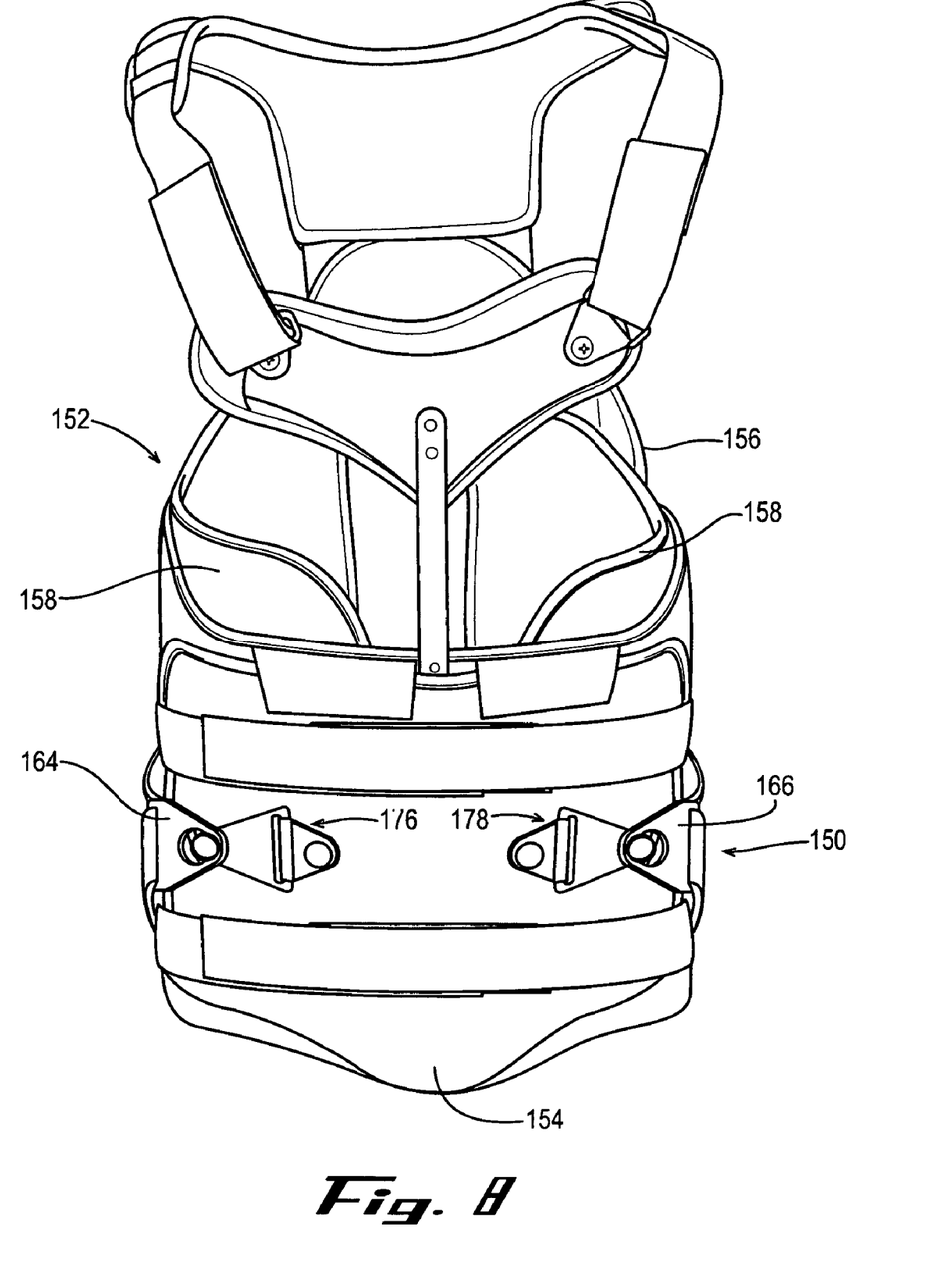
FIGS. 8-11 show a brace and strap system in accordance with an alternate embodiment of the invention.
Figure 9:
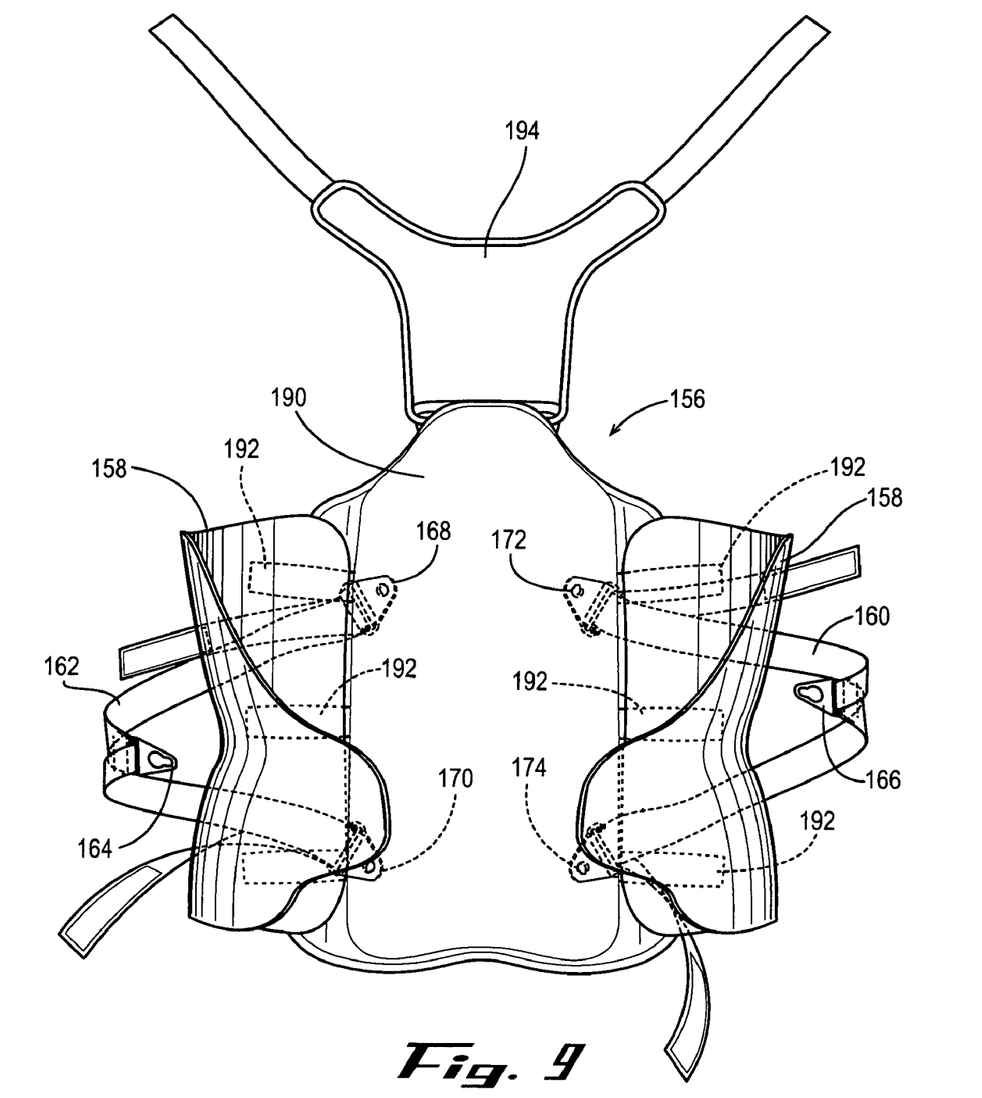
Figure 10:
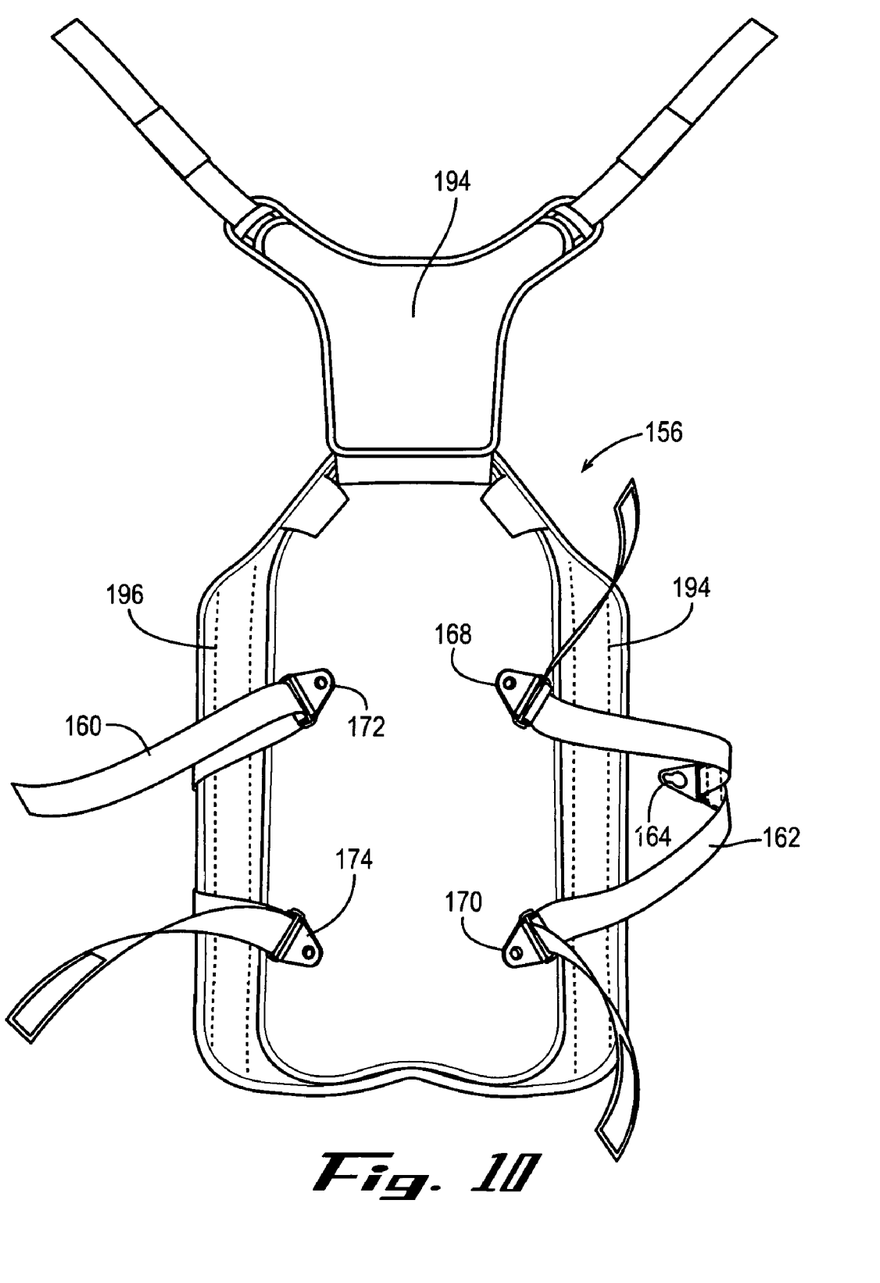
Figure 11:
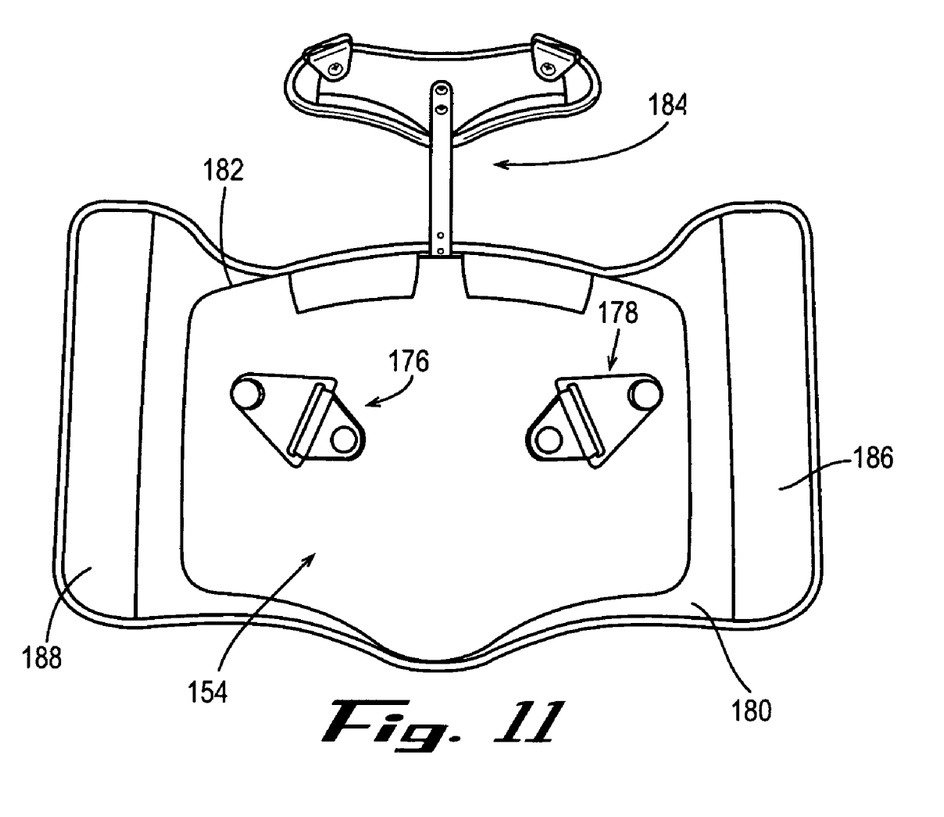

FIGS. 8-11

With reference to FIGS. 8-11, there is shown an alternate embodiment of a brace and strap system having a strap system 150 and a brace 152 having an anterior support 154, a posterior support 156, and a pair of overlapping supports 158.

The strap system 150 preferably corresponds to the strap system 10 described herein. In this regard, the strap system 150 preferably includes a pair of straps 160 and 162, a pair of buckles 164 and 166 fixedly secured on the straps 160 and 162, slides 168, 170, 172, and 174 attached to exterior portions of the posterior support 154, and latch members 176 and 178 attached to exterior portions of the anterior support 154.

The depicted brace 152 preferably corresponds to the brace described and shown in commonly assigned and co-pending application Ser. No. 10/738,796, entitled SPINAL BRACE, filed Dec. 17, 2003, incorporated herein by reference in its entirety.

The anterior support 154 preferably includes a foam body 180 having a pocket 182 for receiving a rigid splint. The foam body 180 is preferably formed of a soft breathable material laminated to a foam and having an outer surface provided by a flexible loop material suitable for releasably engaging a flexible hook material. A sternal extension 184 member is preferably releasably mountable to the rigid splint as by use of screw or other fasteners. The body 180 also preferably includes opposite side extensions 186 and 188 which extend from the side edges thereof. The extensions 186 a88 116 are preferably made of the same material as the body 180 and include internal rigid stays running substantially the length of the extensions.

The posterior support 156 preferably includes a foam body 190 having a pocket for receiving a rigid splint. The body 190 is preferably formed of a soft breathable material laminated to a foam and having an outer surface provided by a flexible loop material suitable for releasably engaging a flexible hook material.

A plurality of strips 192 of hook material extend from opposite side edges of the body 190. The body 190 also preferably includes opposite side extensions 194 and 196 which extend from the side edges thereof. The extensions 194 and 196 are preferably made of the same material as the body 190 and include internal rigid stays running substantially the length of the extensions. A plurality of slits are preferably formed at the junctures between the side extensions 194 and 196 and their respective side edges adjacent each of the strips 192. The strips 192 are preferably used to secure the overlap supports 158. A thoracic extension 194 is preferably installed on the posterior support 156 to provide additional bracing.

The overlapping supports 158 are each preferably of lightweight laminate construction made of a flexible foam material, a rigid plastic strip, and a rigid plastic sheet material sandwiched between a pair of soft flexible sheet materials to yield a substantially rigid laminate material shaped to substantially conform to a side portion of a patient.

The foam material may preferably be a sheet of about ⅛ inch thick closed cell foam material. The rigid plastic strip, for example, may preferably be a strip of about 1/16 inch thick ABS plastic. The sheet materials may preferably be provided as by a sheet of about 1/16 inch thick low density polyethylene. The supports 158 are preferably made as by vacuum molding with adhesive placed between each layer. The supports 158 may be heated if desired, as by a heat gun or oven, to soften them so that they may be custom fit to the patient. In configuring or custom-fitting the supports 158, it is desired that the supports 158 be shaped so as to wrap around the iliac crests of the patient and over the anterior superior iliac spines of the patient.

The foregoing description of certain exemplary embodiments of the present invention has been provided for purposes of illustration only, and it is understood that numerous modifications or alterations may be made in and to the illustrated embodiments without departing from the spirit and scope of the invention as defined in the following claims.

What is claimed is:

1. A brace, comprising:
  a posterior support having a substantially rigid posterior splint;
  an anterior support having a substantially rigid anterior splint;
  first and second overlapping supports releasably attachable to the posterior support, each overlapping support having a substantially rigid splint; and
  a strap system for securing the supports in fitting engagement with the body parts of the user, wherein the strap system includes a first strap and a first buckle located on the first strap, a second strap and a second buckle located on the second strap, a plurality of slides secured to a portion of the posterior support for receiving the straps, a first latch member secured to a first portion of the anterior support for releasably engaging the first buckle, and a second latch member secured to a second portion of the anterior support for releasably engaging the second buckle.

2. The brace of claim 1, wherein the first overlapping support is positionable relative to the posterior and the anterior supports when the orthosis is installed on a user so that the substantially rigid splint of the first overlapping support overlaps at least a portion of the posterior splint and the anterior splint, and the second overlapping support is positionable relative to the posterior and the anterior supports when the orthosis is installed on a user so that the substantially rigid splint of the second overlapping support overlaps at least a portion of the posterior splint and at least a portion of the anterior splint.

3. The brace of claim 1, wherein the first buckle is secured to the first strap and the second buckle is secured to the second strap.

4. The brace of claim 1, wherein the plurality of slides comprises a first pair of slides for receiving the first strap and a second pair of slides for receiving the second strap.

5. The brace of claim 1, wherein the first buckle includes a latching aperture and the first latch member includes a projection for releasably engaging the latching aperture.

6. The brace of claim 1, wherein the overlapping supports each comprise a laminate made of a flexible foam material, a rigid plastic strip, and a rigid plastic sheet material sandwiched between a pair of soft flexible sheet materials to yield a substantially rigid laminate material shaped to substantially conform to a side portion of a patient.

* * * * *